United States Patent
Liu et al.

(10) Patent No.: US 10,308,658 B2
(45) Date of Patent: Jun. 4, 2019

(54) SALT OF EGFR INHIBITOR, CRYSTALLINE FORM AND USES THEREOF

(71) Applicant: SUNSHINE LAKE PHARMA CO., LTD., Dongguan, Guangdong (CN)

(72) Inventors: Bing Liu, Dongguan (CN); Weihong Zhang, Dongguan (CN); Yingjun Zhang, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 15/769,065

(22) PCT Filed: Oct. 18, 2016

(86) PCT No.: PCT/CN2016/102453
§ 371 (c)(1),
(2) Date: Apr. 17, 2018

(87) PCT Pub. No.: WO2017/067447
PCT Pub. Date: Apr. 27, 2017

(65) Prior Publication Data
US 2018/0298019 A1 Oct. 18, 2018

(30) Foreign Application Priority Data
Oct. 19, 2015 (CN) .......................... 2015 1 0677405

(51) Int. Cl.
| | | |
|---|---|---|
| C07D 491/056 | (2006.01) |
| A61K 31/517 | (2006.01) |
| A61K 45/06 | (2006.01) |
| A61K 31/337 | (2006.01) |
| A61K 31/427 | (2006.01) |
| A61K 31/436 | (2006.01) |
| A61K 31/5355 | (2006.01) |
| A61K 31/573 | (2006.01) |
| A61K 31/7072 | (2006.01) |
| A61K 35/04 | (2006.01) |
| A61P 35/04 | (2006.01) |

(52) U.S. Cl.
CPC ........ *C07D 491/056* (2013.01); *A61K 31/517* (2013.01); *A61K 45/06* (2013.01); *A61P 35/04* (2018.01); *A61K 31/337* (2013.01); *A61K 31/427* (2013.01); *A61K 31/436* (2013.01); *A61K 31/5355* (2013.01); *A61K 31/573* (2013.01); *A61K 31/7072* (2013.01); *A61K 2300/00* (2013.01)

(58) Field of Classification Search
CPC .............. A61K 2300/00; A61K 31/517; A61K 31/337; A61K 31/427; A61K 31/436; A61K 31/5355; A61K 31/573; A61K 31/7072; A61K 45/06; A61P 35/04; C07D 491/056
See application file for complete search history.

(56) References Cited

U.S. PATENT DOCUMENTS 9,181,277 B2  11/2015  Zhang et al.

FOREIGN PATENT DOCUMENTS

| CN | 103102344 A | * | 5/2013 |
|---|---|---|---|
| CN | 105294715 B | | 12/2017 |
| CN | 105294716 B | | 12/2017 |
| CN | 105294717 B | | 12/2017 |
| CN | 105294719 | | 12/2017 |
| CN | 105461729 | | 12/2017 |
| CN | 105294718 | | 1/2018 |

OTHER PUBLICATIONS

Eng. Translation of the Abstract of CN105461729.
Eng. Translation of the Abstract of CN105294719.
Eng. Translation of the Abstract of CN105294718.
Eng. Translation of the Abstract of CN105294717.
Eng. Translation of the Abstract of CN105294716.
Eng. Translation of the Abstract of CN105294715.
International Search Report of PCT/CN2016/102453.
Written Opinion of PCT/CN2016/102453.

* cited by examiner

*Primary Examiner* — Erich A Leeser
(74) *Attorney, Agent, or Firm* — Kam Wah Law (57) ABSTRACT

The invention relates to a salt, a hydrate or a crystalline form of an EGFR inhibitor, and use thereof. Specifically it relates to 4-[(3-chloro-4-fluorophenyl)amino]-7-methoxy-6-[3-[(1R,6S)-2,5-dioxa-8-azabicyclo [4.3.0] nonan-8-yl] propoxy] quinazoline dimethanesulfonate, hydrate and a crystalline form thereof; the invention also relates to a preparation method of the crystalline form disclosed herein, a pharmaceutical composition containing the crystalline form, and uses thereof for treating proliferative disorders.

20 Claims, 3 Drawing Sheets

SALT OF EGFR INHIBITOR, CRYSTALLINE FORM AND USES THEREOF

CROSS-REFERENCE TO RELATED APPLICATIONS

This is a U.S. national stage application of the International Patent Application No. PCT/CN2016/102453, filed Oct. 18, 2016, which claims priorities to Chinese Patent Application No. 201510677405.3, filed Oct. 19, 2015, both of which are incorporated herein by reference in their entirety.

FIELD

The invention relates to 4-[(3-chloro-4-fluorophenyl)amino]-7-methoxy-6-[3-[(1R,6S)-2,5-dioxa-8-azabicyclo[4.3.0]nonan-8-yl]propoxy]quinazoline dimethanesulfonate, a hydrate thereof and a crystalline form thereof; the invention also relates to the preparation methods of the monohydrate of the salt and the crystalline form thereof disclosed herein, the pharmaceutical composition containing the salt, the hydrate of the salt or the crystalline form of the monohydrate of the salt disclosed herein, and the use of the pharmaceutical composition.

BACKGROUND

Epidermal growth factor receptor (EGFR), a kind of receptor tyrosine kinases, is over expressed and/or mutated in most tumors. It can control the tumor growth by signal transduction and is closely related to the angiogenesis, invasion and metastasis of tumor. EGFR is an important regulatory factor in cell growth, differentiation and survival, members of which include erbB-1 (EGFR, HER1), erbB-2 (EGFR, HER2), erbB-3 (EGFR, HER3) and erbB-4 (EGFR, HER4), and these members have similar structure consisting of extracellular receptor ligand domain, single-strand transmembrane domain and highly conserved protein tyrosine kinase domain, with the function of the receptor as well as the ability of converting extracellular signal into intracellular effect directly as a novel transmembrane transit mode. Once combined with specific ligand, EGFR is activated by autophosphorylation of relative tyrosine kinase, resulting in activation of intracellular signal transduction pathways. These pathways of signal transduction include: activation of Ras protein kinase and mitogen-activated protein kinase (MAPK) leads to activation of multiple proteins in the nucleus involving cyclin D1, thereby leading to DNA synthesis, cell growth and differentiation. Excessive activation of the growth factor receptors makes cell proliferation out of control, therefore, induces various types of excess proliferative diseases, such as non-small cell lung cancer, cancer of breast and head, etc. Since inhibition of epidermal growth factor receptor tyrosine kinases has been proved to be of value in regulating cell replication out of control, it becomes the therapeutic target for novel antitumor drugs.

Chinese patent CN 103102344 A (publication number) have disclosed the structure of 4-[(3-chloro-4-fluorophenyl)amino]-7-methoxy-6-[3-[(1R,6S)-2,5-dioxa-8-azabicyclo[4.3.0]nonan-8-yl]propoxy]quinazoline in example 6 of specification, page 57, and the structure is shown as Formula (II). The compound of Formula (II) has a high inhibition activity against EGFR, and can be used for treating proliferative disorders.

However, the patent described above has not disclosed salt of the compound of Formula (II), hydrate of the salt and crystalline form thereof.

SUMMARY OF THE INVENTION

The invention provides crystalline form I of 4-[(3-chloro-4-fluorophenyl)amino]-7-methoxy-6-[3-[(1R,6S)-2,5-dioxa-8-azabicyclo[4.3.0]nonan-8-yl]propoxy]quinazoline dimethanesulfonate monohydrate, which has good stability, and higher bioavailability than the compound of Formula (II).

The following content merely summarizes certain aspects of the invention and is not intended to be limiting in nature. These aspects and other aspects and embodiments are described more fully below. All references of this specification are incorporated herein by reference in their entirety. In the event that one or more of the incorporated literatures or patents differ from or contradict this application, this application controls.

Provided herein are 4-[(3-chloro-4-fluorophenyl)amino]-7-methoxy-6-[3-[(1R,6S)-2,5-dioxa-8-azabicyclo[4.3.0]nonan-8-yl]propoxy]quinazoline dimethanesulfonate, a monohydrate thereof and crystalline form I of the monohydrate, which can be used for treating proliferative disorders. Also provided herein are preparation method of crystalline form I and method of using crystalline form I for the treatment of proliferative disorders in mammals, especially humans, and pharmaceutical composition containing crystalline form I and use thereof.

In one aspect, provided herein is a compound having Formula (I):

In other aspect, provided herein is a hydrate of the compound having Formula (I).

In certain embodiments, wherein the hydrate is a monohydrate having Formula (III):

(III)

In other aspect, provided herein is a crystalline form of a monohydrate of a compound having formula (I):

(I)

wherein the crystalline form is form I having one or more of following characteristics:

i) an X-ray powder diffraction (XRPD) pattern comprising peaks expressed in degrees 2θ at 14.88°±0.2°, 18.05°±0.2°, 20.84°±0.2°, 21.34°±0.2°, 24.39°±0.2° and 25.18°±0.2°; or/and ii) the following structure parameters analyzed from monocrystalline:
Crystallographic System: monoclinic system;
Space Groups: C2/c;
Cell Parameters: a=27.3004(5) Å, α=90°,
b=16.2882(3) Å, β=103.3439(17)°,
c=14.3529(2) Å, γ=90°;
Volume: 6210.01(18) Å$^3$;
Molecules number of 8.
each unit cell (Z):

In certain embodiments, the crystalline form disclosed herein has an X-ray powder diffraction (XRPD) pattern comprising peaks expressed in degrees 2θ at 9.47±0.2°, 14.88°±0.2°, 16.58°±0.2°, 17.15°±0.2°, 17.46°±0.2°, 18.05°±0.2°, 20.46°±0.2°, 20.84°±0.20, 21.34°±0.2°, 22.710°±0.2°, 23.16°±0.2°, 24.39°±0.2°, 25.18°±0.2°, 25.46°±0.2°, 26.29°±0.2° and 28.01°±0.2°.

In certain embodiments, the crystalline form disclosed herein has an X-ray powder diffraction (XRPD) pattern comprising peaks expressed in degrees 2θ at 6.36°±0.2°, 6.66°±0.2°, 9.47°±0.2°, 10.82°±0.2°, 11.70°±0.2°, 13.31°±0.2°, 14.88°±0.2°, 15.86°±0.2°, 16.58°±0.2°, 17.15°±0.2°, 17.46°±0.2°, 18.05°±0.2°, 19.30°±0.2°, 20.46°±0.2°, 20.840°±0.2°, 21.34°±0.2°, 21.76°±0.2°, 22.28°±0.2°, 22.71°±0.2°, 23.16°±0.2°, 24.07°±0.2°, 24.39°±0.2°, 25.18°±0.2°, 25.46°±0.2°, 26.29°±0.2°, 26.78°±0.2°, 27.15°±0.2°, 28.010°±0.2°, 28.80°±0.2°, 29.77°±0.2°, 30.44°±0.2°, 31.06°±0.2°, 32.05°±0.2°, 33.01°±0.2°, 33.51°±0.2°, 33.84°±0.2°, 34.90°±0.2°, 38.03°±0.2°, 38.58°±0.2° and 39.48°±0.2°.

Figure 1:
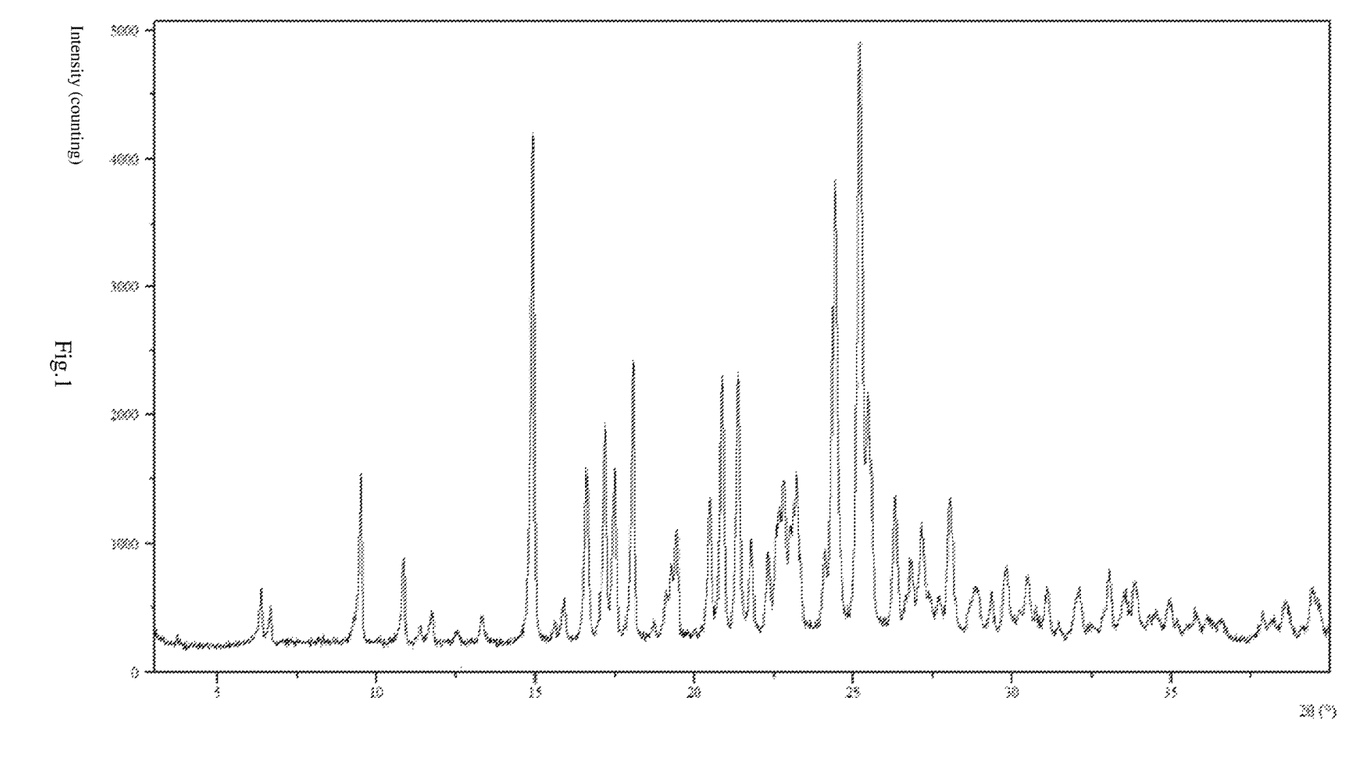
FIG. 1 shows an X-ray powder diffraction (XRPD) pattern of crystalline form I according to example 1.

In certain embodiments, the crystalline form disclosed herein has an X-ray powder diffraction (XRPD) pattern substantially the same as shown in FIG. 1.

In certain embodiments, the crystalline form disclosed herein has a weight loss ratio of 3.234%±0.1% measured by thermogravimetric analysis in a temperature ranged from 25° C. to 150° C.

Figure 2:
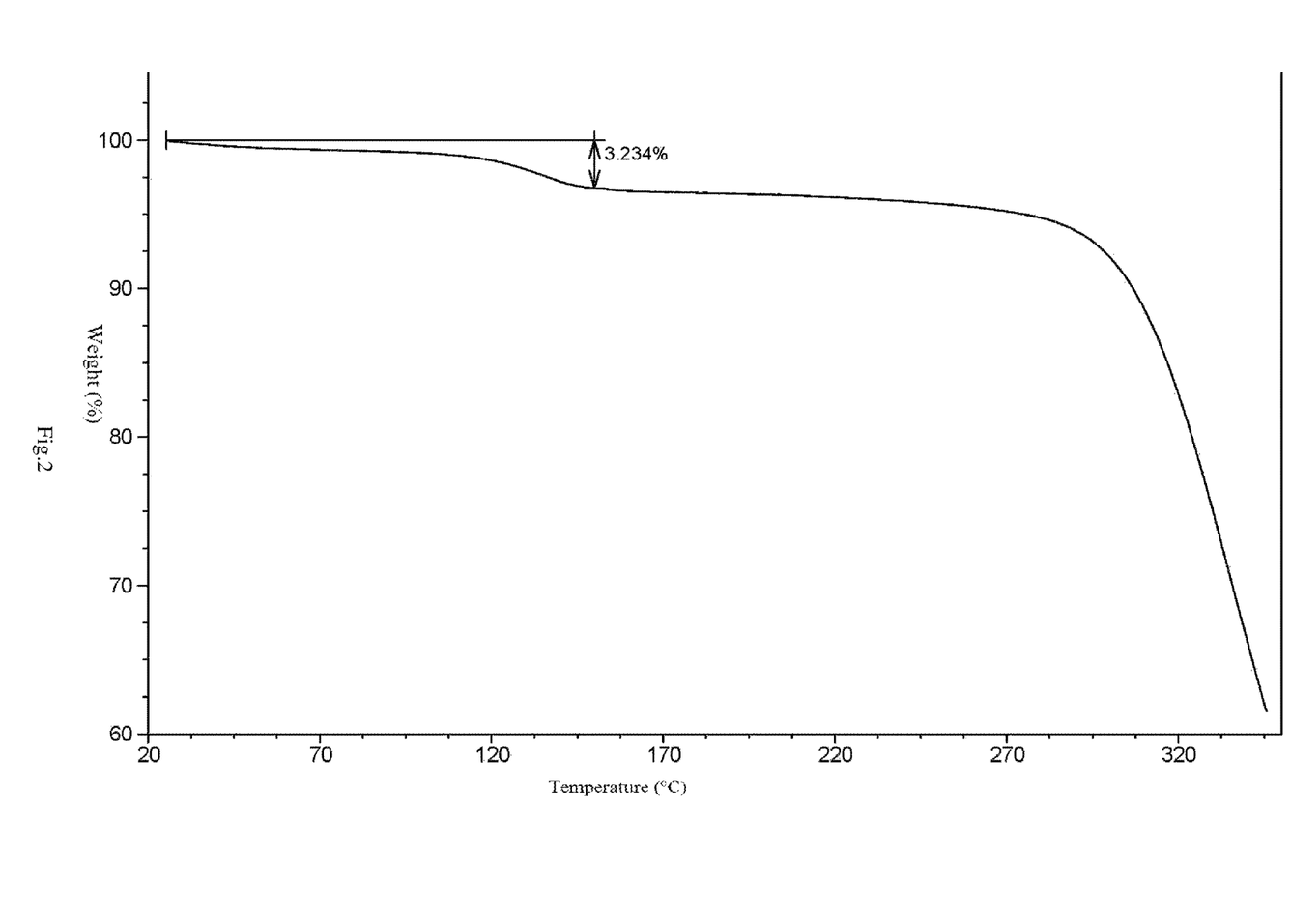
FIG. 2 shows a thermogravimetric analysis (TGA) curve of crystalline form I according to example 1.

In certain embodiments, the crystalline form disclosed herein has a thermogravimetric analysis curve as shown in FIG. 2.

Figure 3:
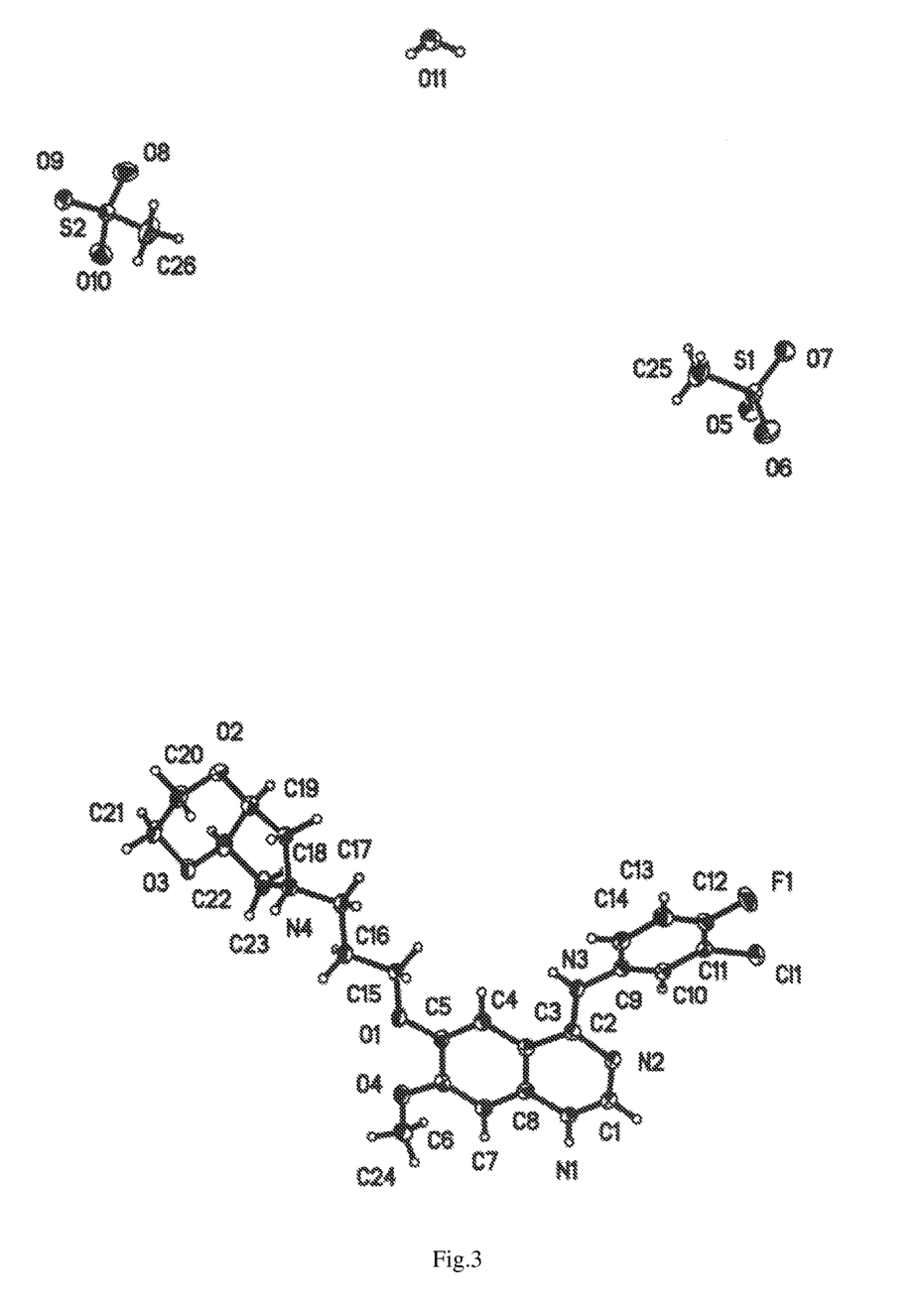
FIG. 3 shows a single-crystal structure of crystalline form I of the invention.

In certain embodiments, the crystalline form disclosed herein has a monocrystalline structure e as shown in FIG. 3.

In other aspect, provided herein is a pharmaceutical composition comprising the compound or the hydrate thereof or crystalline form disclosed herein, or a combination thereof.

In certain embodiments, the pharmaceutical composition further comprises a pharmaceutically acceptable carrier, excipient, diluent, adjuvant, vehicle or a combination thereof.

In certain embodiments, the pharmaceutical composition further comprises a therapeutic agent, and wherein the therapeutic agent is a chemotherapeutic agent used for treating proliferative disease or cancer, an antiproliferative agent, a cytotoxic agent, a signal transduction inhibitor, an agent used for treating non-small cell lung cancer and skin cancer or a combination thereof.

In other embodiments, the pharmaceutical composition disclosed herein, wherein the therapeutic agent is adriamycin, rapamycin, temsirolimus, everolimus, ixabepilone, gemcitabine, cyclophosphamide, dexamethasone, etoposide, fluorouracil, imatinib mesylate, dasatinib, nilotinib, erlotinib, lapatinib, gefitinib, sorafenib, sunitinib, interferon, carboplatin, topotecan, paclitaxel, vinblastine, vincristine, temozolomide, tositumomab, trabedectin, bevacizumab, trastuzumab, cetuximab, panitumumab, icotinib, icotinib hydrochloride, matuzmab, neratinib, canertinib, vandetanib, cediranib, vatalanib, axitinib, motesanib, nimotuzumab, theliatinib, epitinib, simotinib, poziotinib, varlitinib, rociletinib, pelitinib, osimertinib, PKI-166, PD 158780, MDX447, Mab425, HM-61713, TAS-121, seribantumab, naquotinib, or a combination thereof.

In other aspect, provided herein is use of the compound, the hydrate, the crystalline form or the pharmaceutical composition disclosed herein in the manufacture of a medicament for inhibiting EGFR.

In other aspect, provided herein is use of the compound, the hydrate, the crystalline form or the pharmaceutical composition disclosed herein, in the manufacture of a medicament for preventing, treating or lessening the severity of a proliferative disorder in a patient.

In certain embodiments, the use disclosed herein, wherein the proliferative disorder is metastatic cancer, skin cancer, colon cancer, stomach cancer, bladder cancer, breast cancer, renal cancer, liver cancer, lung cancer, thyroid cancer, brain tumor, cervical cancer, prostate cancer, pancreatic cancer, CNS (central nervous system) cancer, malignant glioma, bone marrow hyperplasia, atherosclerosis or lung fibrosis.

In other aspect, provided herein is the compound, the hydrate, the crystalline form or the pharmaceutical composition disclosed herein for use in inhibiting EGFR.

In other aspect, provided herein is the compound, the hydrate, the crystalline form or the pharmaceutical composition disclosed herein, for use in preventing, treating or lessening the severity of a proliferative disorder in a patient.

In certain embodiments, the compound, the hydrate, the crystalline form, or the pharmaceutical composition disclosed herein, wherein the proliferative disorder is metastatic cancer, skin cancer, colon cancer, stomach cancer, bladder cancer, breast cancer, renal cancer, liver cancer, lung cancer, thyroid cancer, brain tumor, cervical cancer, prostate cancer, pancreatic cancer, CNS (central nervous system) cancer, malignant glioma, bone marrow hyperplasia, atherosclerosis or lung fibrosis.

In other aspect, provided herein is a method of inhibiting EGFR in a subject, comprising administering to the subject a therapeutically effective amount of the compound, the hydrate, the crystalline form, or the pharmaceutical composition disclosed herein.

In other aspect, provided herein is a method of preventing, treating or lessening the severity of a proliferative disorder in a patient, comprising administering to the patient a therapeutically effective amount of the compound, the hydrate, the crystalline form, or the pharmaceutical composition disclosed herein.

In certain embodiments, the method disclosed herein, wherein the proliferative disorder is metastatic cancer, skin cancer, colon cancer, stomach cancer, bladder cancer, breast cancer, renal cancer, liver cancer, lung cancer, thyroid cancer, brain tumor, cervical cancer, prostate cancer, pancreatic cancer, CNS (central nervous system) cancer, malignant glioma, bone marrow hyperplasia, atherosclerosis or lung fibrosis.

Definitions and General Terminology

Unless defined otherwise, all technical and scientific terms used herein have the same meaning as is commonly understood by one skilled in the art to which this invention belongs. All patents and publications referred to herein are incorporated by reference in their entirety. Although many methods and materials similar or equivalent to those described herein could be used in the practice or test of the present invention, the preferred methods, equipments and materials are described in the invention.

The compound of Formula (I) has amorphous form, crystalline form, solvate, and polymorphic form. Especially, the solvate disclosed herein is a hydrate. The hydrate of compound of Formula (I) has amorphous form, crystalline form or polymorphic form.

In certain embodiments, the compound or hydrate of the invention exists in crystalline form preferably having at least 50% crystallinity, more preferably having at least 60% crystallinity, still more preferably having at least 70% crystallinity, and most preferably having at least 80% crystallinity. Crystallinity can be assessed by conventional X-ray diffraction techniques.

In other embodiments, the compound or hydrate of the invention has a crystallinity ranged from 50%, 60%, 70%, 80% or 90% to 95%, 96%, 97%, 98%, 99% or 100%.

The term "crystalline form" refers to a solid having a highly regular chemical structure, including, but not limited to, a single-component or multiple-component crystal, and/or a polymorph, a solvate, a hydrate, a clathrate, a co-crystal, a salt of a compound, solvates of salts, hydrates of salts. Crystalline forms of a substance can be obtained by a number of methods as known in the art. Such methods include, but are not limited to, melt crystallization, melt cooling, solvent crystallization, crystallization in confined spaces such as, e.g., in nanopores or capillaries, crystallization on surfaces or templates such as, e.g., on polymers, crystallization in the presence of additives, such as, e.g., co-crystal counter-molecules, desolvation, dehydration, rapid evaporation, rapid cooling, slow cooling, vapor diffusion, sublimation, reaction crystallization, anti-solvent addition, grinding and solvent-drop grinding. The crystalline form includes anhydrous crystalline form, partially crystalline form, mixture of crystalline forms, hydrate crystalline form and solvate crystalline form.

"Amorphism" or "amorphous form" refers to substance forming by particle (such as molecule, atom, ion) arranged in no periodic in three-dimensional space, which is characterized by a diffused X-ray powder diffraction pattern with no sharp peaks. Amorphism is a special physical form of solid substance, the ordered structural characteristics in a part of amorphous substance imply there are innumerable links between amorphous substance and crystal substance. Amorphous form of a substance can be obtained by a number of methods as known in the art. These methods include, but are not limited to, rapid freezing method, anti-solvent flocculence, ball-milling method, spray drying method, freeze-drying method, wet granulating method and solid dispersion technique, and the like.

The term "solvent", as used herein, means a substance, typically a liquid, that is capable of completely or partially dissolving another substance, typically a solid. Solvents for the practice of the invention include, but are not limited to, water, acetic acid, acetone, acetonitrile, benzene, chloroform, tetrachloromethane, dichloromethane, dimethyl sulfoxide, 1,4-dioxane, ethanol, ethyl acetate, butanol, tert-butanol, N,N-dimethylacetamide, N,N-dimethylformamide, formamide, formic acid, heptane, hexane, isopropanol, methanol, methyl ethyl ketone, 1-methyl-2-pyrrolidone, mesitylene, nitromethane, polyethylene glycol, propanol, pyridine, tetrahydrofuran, toluene, xylene, mixtures thereof, etc.

The term "solvate" as used herein, means having on a surface, in a lattice or on a surface and in a lattice of the crystal, solvents for the practice of the invention include, but are not limited to, water, acetic acid, acetone, acetonitrile, benzene, chloroform, tetrachloromethane, dichloromethane, dimethyl sulfoxide, 1,4-dioxane, ethanol, ethyl acetate, butanol, tert-butanol, N,N-dimethylacetamide, N,N-dimethylformamide, formamide, formic acid, heptane, hexane, isopropanol, methanol, methyl ethyl ketone, 1-methyl-2-pyrrolidone, mesitylene, nitromethane, polyethylene glycol, propanol, pyridine, tetrahydrofuran, toluene, xylene, mixtures thereof, etc. A specific example of a solvate is a hydrate, wherein the solvent on the surface, in the lattice or on the surface and in the lattice of the crystal, is water. Hydrates may or may not have solvents other than water on the surface, in the lattice or on the surface and in the lattice of a substance.

Unless otherwise specified, when referring to "solvates" and "hydrates", the invention is intended to include stoichiometric and non-stoichiometric "solvates" and "hydrates".

Stoichiometric solvates have a fixed ratio of solvent molecules to the molecules of the compound. This is typically due to a bonding interaction between the solvent and the compound molecule. In non-stoichiometric solvates, the solvent is not present in a fixed ratio to the molecules of the compound and the amount of the solvent often can vary. In a non-stoichiometric solvate, the solvent is often present in the void spaces or channels within the crystalline lattice.

Stoichiometric hydrates have a fixed ratio of water molecules to the molecules of the compound. This is typically due to a bonding interaction between the water and the compound molecule. In non-stoichiometric hydrates, water is not present in a fixed ratio to the molecules of the compound and the amount of water often can vary. In a non-stoichiometric hydrate, the water is often present in the void spaces or channels within the crystalline lattice.

The compound or hydrate of the invention preferably exists in separated substantially pure form.

The invention also relates to the solid state physical properties of the compound, hydrate or crystalline form of the invention. These properties can be influenced by controlling the conditions under which the salt or crystalline form of the invention is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid or the bioavailability of the pharmaceutical compound. The rate of dissolution of an active ingredient in a patient's stomach fluid can have therapeutic consequences since it imposes an upper limit on the rate at which an orally-administered active ingredient can reach the patient's bloodstream.

For example, different crystal forms or amorphous form of the same drug may have substantial differences in such pharmaceutically important properties as dissolution rates and bioavailability. Likewise, different crystals or amorphous form may have different processing properties, such as hydroscopicity, flowability, and the like, which could affect their suitability as active pharmaceuticals for commercial production.

The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic form of a substance.

Crystalline form or amorphism can be identified through multiple technological means, such as X-ray powder diffraction (XRPD), infrared spectroscopy (IR), melting point, differential scanning calorimetry (DSC), thermogravimetry analysis (TGA), nuclear magnetic resonance, raman spectroscopy, single-crystal X-ray diffraction, solution calorimetry, scanning electron microscope (SEM), quantitative analysis, solubility, dissolution velocity, etc.

Some information such as change in crystalline form, crystallinity, crystal structure state and so on can be obtained through detection of X-ray powder diffraction (XRPD) which is a common method used for identifying crystalline form. The peak position of XRPD spectra mainly depends on the crystal structure, which is relatively insensitive to experimental details, and the relative peak height depends on many factors related to sample preparation and the geometry of the instrument. Thus, in some embodiments, the crystalline form disclosed herein is characterized by an X-ray powder diffraction pattern having some peaks in certain positions, which is substantially the same as the XRPD pattern provided in appended figures of the present invention. Meanwhile, the measurement of 2θ in XRPD pattern could have some experimental error, for example the measurements of 2θ in XRPD pattern could be different because of different instruments and different samples. Therefore, the value of 2θ is not absolute. According to the state of the instrument for the experiment disclosed herein, the error margin in 2θ of the characteristic peaks is ±0.2°.

Thermogravimetric analysis (TGA) is a technology used for measuring the quality change of a substance which varies with temperature of a substance under program control, which can apply to detecting the process of the solvent loss in the crystal, sublimation and dissociation of the sample, and the crystal water and the crystal solvent contained in crystal may be speculated through analysis of the detection results. The measurement of quality change described in TGA curve depends on many factors related to sample preparation and instrument geometry, etc, which could be different because of different instruments and different samples. According to the state of the instrument for the experiment disclosed herein, the error margin of the quality change is ±0.1%.

As used herein, the value of 2θ described in an X-ray powder diffraction pattern is recorded in degree (°).

As used herein, term "substantially the same as shown in a figure" refers to an X-ray powder diffraction (XRPD) pattern, or a differential scanning calorimetry (DSC) thermogram, or a Raman spectrogram, or a Fourier transform infrared spectrogram having at least 50%, at least 60%, at least 70%, at least 80%, at least 90%, at least 95%, or at least 99% of the peaks shown in the figure.

As used herein, when referring to a spectrum and/or to data presented in a graph, the term "peak" refers to a feature that one skilled in the art would recognize as not attributable to background noise.

Whenever a number having a value N is disclosed, any number having the value N±0.01, N±0.02, N±0.03, N±0.05, N±0.07, N±0.08, N±0.1, N±0.15, N±0.2, N±, N±2, N±1.5, N±3, N±4, N±5, N±6, N±7, N±8, N±9, N±10, N±15, N±20 is specifically disclosed, wherein "±" refers to plus or minus. Whenever a numerical range with a lower limit, RL, and an upper limit, RU, is disclosed, any number falling within the range is specifically disclosed.

The compound having Formula (II) of the invention is prepared according to the synthetic method of example 6 described in patent CN 103102344 A (publication number), and is named 4-[(3-chloro-4-fluorophenyl)amino]-7-methoxy-6-[3-[(1R,6S)-2,5-dioxa-8-azabicyclo [4.3.0] nonan-8-yl]propoxy]quinazoline.

Unless otherwise specified, the compound of the invention refers to the compound having Formula (I) or a monohydrate thereof; the crystalline form I refers to crystalline form I of the monohydrate of the compound having Formula (I).

The compound of Formula (I) is the dimethanesulfonate of the compound having Formula (II), which is named: 4-[(3-chloro-4-fluorophenyl)amino]-7-methoxy-6-[3-[(1R, 6S)-2,5-dioxa-8-azabicyclo[4.3.0]nonan-8-yl]propoxy]quinazoline dimethanesulfonate. The monohydrate of the compound having Formula (I) is 4-[(3-chloro-4-fluorophenyl) amino]-7-methoxy-6-[3-[(1R,6S)-2,5-dioxa-8-azabicyclo [4.3.0]nonan-8-yl]propoxy]quinazoline dimethanesulfonate monohydrate. crystalline form I of the monohydrate of the compound having Formula (I) is crystalline form I of 4-[(3-chloro-4-fluorophenyl)amino]-7-methoxy-6-[3-[(1R, 6S)-2,5-dioxa-8-azabicyclo[4.3.0]nonan-8-yl]propoxy]quinazoline dimethanesulfonate monohydrate. They are substantially existing in pure crystalline form.

As used herein, "substantially pure" refers to a compound/salt/crystalline form that is substantially free of one or more other compounds/salts/crystalline forms, i.e., the compound/salt/crystalline form has a purity of at least about 80%, at least about 85%, at least about 90%, at least about 93%, at least about 95%, at least about 98%, at least about 99%, at least about 99.5%, at least about 99.6%, at least about 99.7%, at least about 99.8%, or at least about 99.9%; or the compound/salt/crystalline form contains less than 20%, less than 10%, less than 5%, less than 3%, less than 1%, less than 0.5%, less than 0.1%, or less than 0.01% of the one or more other compounds/salts/crystalline forms, based on the total volume or weight of the compound/salt/crystalline form and the one or more other compounds/salts/crystalline forms.

As used herein, a compound/salt/crystalline form that is "substantially free" of one or more other compounds/salts/crystalline forms refers to the compound/salt/crystalline form containing less than 20%, less than 10%, less than 5%, less than 4%, less than 3%, less than 2%, less than 1%, less than 0.5%, less than 0.1%, or less than 0.01% of the one or more other compounds/salts/crystalline forms, based on the total volume or weight of the compound/salt/crystalline form and the one or more other compounds/salts/crystalline forms.

As used herein, the term "relative intensity" refers to the intensity of a peak with respect to the intensity of the strongest peak in the X-ray powder diffraction (XRPD) pattern which is regarded as 100%.

As used herein, all numbers disclosed herein are approximate values, regardless whether the word "about" is used in connection therewith, which means within 10%, suitably within 5% and particularly within 1% of a given value or range. Alternatively, the term "about" means within an acceptable standard error of the mean, when considered by one of the ordinary skill in the art. Therefore, whenever a number having a value N is disclosed, any number having the value N+/−1%, N+/−2%, N+/−3%, N+/−5%, N+/−7%, N+/−8% or N+/−10% is specifically disclosed, wherein "+/−" refers to plus or minus.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, "patient" refers to a human (including adults and children) or other animal. In one embodiment, "patient" refers to a human.

The term "comprise" is an open expression, it means comprising the contents disclosed herein, but don't exclude other contents.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compound of Formula (I) or (III) are within the scope disclosed herein.

Unless otherwise stated, all tautomeric forms of the compound of Formula (I) or (III) disclosed herein are within the scope of the invention. Additionally, unless otherwise stated, the structure of compound of Formula (I) or (III) depicted herein is also meant to represent compounds that differ only in the presence of one or more isotopically enriched atoms.

Stereochemical definitions and conventions used herein generally follow S. P Parker, Ed., *McGraw-Hill Dictionary of Chemical Terms* (1984) McGraw-Hill Book Company, New York and Eliel, E. and Wilen, S., "*Stereochemistry of Organic Compounds*", John Wiley & Sons, Inc., New York, 1994. The compound of Formula (I) or (III) exists asymmetric centers or chiral centers, therefore has different stereoisomers. It is intended that all stereoisomeric forms of the compound of Formula (I) or (III), including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

Pharmaceutical Compostions of Salt or Hydrate or Crystalline Form of the Invention, Preparations, Administrations and Uses Thereof As described above, the pharmaceutically acceptable composition disclosed herein comprises the compound, hydrate or crystalline form disclosed herein, or a combination thereof, and optionally pharmaceutically acceptable carrier, an adjuvant, or a vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Content of the active ingredient in pharmaceutical composition is an amount of 1-99 wt %, 1-95 wt %, 1-90 wt %, 1-85 wt %, 1-80 wt %, 1-75 wt %, 1-70 wt %, 1-65 wt %, 1-60 wt %, 1-55 wt %, 1-50 wt %, 1-45 wt %, 1-40 wt %, 1-35 wt %, 1-30 wt % %, 1-25 wt %, 1-20 wt %, 1-15 wt %, 1-10 wt. %, 1-5 wt %. As is described: *In Remington: The Science and Practice of Pharmacy,* 21st ed., 2005, Lippincott Williams & Wilkins, Philadelphia, and Swarbrick et al., *Encyclopedia of Pharmaceutical Technology,* eds. 1988-1999, Marcel Dekker, New York, both of which are herein incorporated by reference in their entireties, discloses various carriers used in formulating pharmaceutically acceptable compositions and known techniques for the preparation thereof. Except insofar as any conventional carrier medium incompatible with the compound, hydrate or crystalline form disclosed herein, such as by producing any undesirable biological effect or otherwise interacting in a deleterious manner with any other components of the pharmaceutically acceptable composition, its use is contemplated to be within the scope of this invention.

Some non-limiting examples of materials which can serve as pharmaceutically acceptable carriers include ion exchangers; aluminium; aluminum stearate; lecithin; serum proteins such as human serum albumin; buffer substances such as phosphates; glycine; sorbic acid; potassium sorbate; partial glyceride mixtures of saturated vegetable fatty acids; water; salts or electrolytes such as protamine sulfate, disodium hydrogen phosphate, potassium hydrogen phosphate, sodium chloride and zinc salts; colloidal silica; magnesium trisilicate; polyvinyl pyrrolidone; polyacrylates; waxes; polyethylene-polyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The compositions disclosed herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection and infusion techniques. In some embodiments, the compositions are administered orally, intraperitoneally or intravenously. Sterile injectable forms of the compositions disclosed herein include aqueous and oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that include water, Ringer's solution and isotonic sodium chloride solution. In addition, sterile, non-volatile oil can be conventionally employed as a solvent or suspending medium.

For this purpose, any bland non-volatile oil includes synthetic mono- or diglycerides. Fatty acids, such as oleic acid and its glyceride derivatives, which are useful in the preparation of injectables, can be used as natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable composition of the present invention can be an acceptable oral formulation for oral administration, including but not limited to, capsules, tablets, pellets, powder, sustained release agents, water suspension or solution. For oral tablets, carriers generally include lactose and corn starch. Lubricants such as magnesium stearate, are typically added. For oral capsule administration, suitable diluents include lactose and dried corn starch. When oral formulation is a water suspension, the active ingredients can be comprised of emulsifier and suspending agent. For these formulations, sweeteners, flavoring agents or colorants can be added.

Liquid formulations for oral administration include, but not limited to, pharmaceutically acceptable emulsions, micro-emulsion, solution, suspension, syrup and elixir. In addition to the active compounds, the liquid dosage forms may contain inert diluents known in the art, for example, water or other solvent, solubilizer and emulsifier, such as ethanol, isopropanol, ethyl carbonate, ethyl acetate, benzyl alcohol, benzyl benzoate, propylene glycol, 1,3-butanediol, dimethylformamide, oils and fats (in particular, cottonseed, groundnut, corn, microbes, olive, castor and sesame oil), glycerin, 2-tetrahydrofuranmethanol, polyethyleneglycol, dehydrated sorbitol fatty acid esters, and their mixtures. Addition to inert diluents, the oral compositions can also contain adjuvants such as wetting agents, emulsifiers or suspending agent, sweeteners, flavorings and fragrances.

In addition, the pharmaceutically acceptable compositions of the present invention can be in the form of a rectal suppository. These can be prepared by mixing the agent with the appropriate non-perfusion adjuvant. The mixture prepared this way is a solid at room temperature, but it becomes a liquid at rectal temperature and releases the drug in the rectum. Such substances include cocoa fat, beeswax, and polyethylene glycol. The pharmaceutically acceptable compositions of the present invention can be used for localized drug delivery, especially when treatment goal is easier to reach with topical drug delivery on certain treatment region or organs, such as disease of eye, skin or intestine. Suitable topical formulations can be prepared and applied to these areas or organs.

Rectal suppositories (see above) or a suitable enema can be applied to the local administration of the lower intestinal tract. Local skin spots can also be medicated the same way. For local administration, the pharmaceutically acceptable compositions can be prepared accordingly to the preparation method into a suitable ointment, the ointment containing the active ingredient suspended in or dissolved in one or more carriers. Localized drug delivery carriers of this invention include, but are not limited to mineral oil, liquid paraffin, white petrolatum, propylene glycol, polyoxyethylene, polyoxypropylene compound, emulsified wax and water. In addition, the pharmaceutically acceptable compositions can be prepared into a suitable lotion or cream, the lotion or cream containing the active ingredient is suspended in or dissolve in one or more pharmaceutically acceptable carriers. A suitable carrier, includes, but is not limited to, mineral oil, Span 60 (sorbitan monostearate), Tween 60 (polysorbate 60), cetyl ester wax, palm alcohol, 2-octyl dodecanol, benzyl alcohol and water.

A pharmaceutically acceptable composition for eye application can be prepared into formulations such as particulate suspensions in isotonic, pH adjusted sterile saline or other aqueous solutions, preferably isotonic solution and pH adjusted sterile saline or other aqueous solutions. The disinfection of preservatives such as benzalkonium chloride can be added to the formulation. In addition, the pharmaceutically acceptable compositions for the eye can be prepared into the ointment such as Vaseline. Administration of a pharmaceutically acceptable composition of the present invention can be applied via the gas solvents or inhalants thorough nose. This composition can be prepared from known formula and technology, or can be prepared as a salt solution using benzyl alcohol or other suitable preservatives, absorption enhancers, fluorocarbons, or other conventional solubilizing agent or dispersing agent to improve the bioavailability.

These injections such as sterile injectable solutions or oily suspensions may be formulated according to techniques known in the art using suitable dispersing or wetting agents and suspending agents. Sterile injection can be a sterile solution or suspension of non-toxic acceptable diluent or solvent, such as 1,3-butanediol. Among the acceptable vehicles and solvents that include water, Ringer's solution, U.S.P. and isotonic sodium chloride solution. Furthermore, sterile non volatile oil can be used as solvent or suspension medium, according to the prior art. For this purpose, any bland non-volatile oil includes synthetic mono- or diglycerides. Fatty acids such as oleic acid and its glyceride derivatives can be used for the preparation of the intravenous injectable.

Injection can be sterile, such as filtration through a sterilization filter, or incorporation of a sterilizing agent in the form of sterile solid compositions. Sterilizing agent can be dissolved in or dispersed in sterile water or sterile injection medium prior to use. In order to prolong the effect of the compounds of the invention, subcutaneous or intra-muscular injection can be used to slow the absorption of compounds. The problem of poor water solubility of the crystal or non-crystalline material can be solved by using liquid suspension. The absorption rate of the compound depends on its dissolution, in turn depends on grain size and crystal shape. In addition, the compound is dissolved or dispersed in the oil excipient to delay absorption of the compound injection.

Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Some non-limiting examples of other biodegradable polymers include poly(orthoesters) and poly(anhydrides). Depot injectable formulations are also prepared by entrapping the compound in liposomes or microemulsions that are compatible with body tissues.

In some embodiments, the composition for rectal or vaginal administration is preferably a suppository. The suppository can be prepared by mixing the compound, hydrate or crystalline form of the present invention with a suitable non-irritative excipient or carrier, such as cocoa butter, polyethylene glycol or suppository wax, they can be solid at room temperature, but liquid at body temperature, and can release an active compound in rectal lumen or vaginal canal.

The solid dosage forms for oral administration include capsules, tablets, pills, powders and granules. In these formulations, the active compounds are mixed with at least one pharmaceutically acceptable inert excipients or carrier, such as sodium citrate or calcium phosphate or filling agents, or (a) fillers such as starch, lactose, sucrose, glucose, mannitol and silicic acid; (b) adhesives such as carboxymethylcellulose, alginates, gelatin, polyethylene pyrrole ketone, sucrose and gum arabic; (c) moisturizing agents such as glycerol; (d) disintegrating agents such as agar, calcium carbonate, potato starch or tapioca starch, alginic acid, certain silicates and sodium carbonate; (e) blocker solution, such as paraffin; (f) absorption promoter such as quaternary ammonium compounds; (g) wetting agents such as decahexanyl alcohol and glycerol monostearate; (h) absorbents such as kaolin and bentonite, (i) lubricants such as talc, calcium stearate, magnesium stearate, solid polyethylene glycol, laurylsodium sulfate, and mixtures thereof. Formulations such as capsules, tablets and pills can contain buffer.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The compound, hydrate or crystalline form disclosed herein can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. Formulations such as capsules, tablets and pills can contain buffer. They may optionally contain pacifying agents and can also be of a composition that they release the active ingredient(s) only, or in other embodiments, in a certain part of the intestinal tract, optionally, in a delayed manner. Examples of embedding compositions that can be used include polymeric substances and waxes.

Dosage forms for topical or transdermal administration of a compound disclosed herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, contemplated herein is the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Preferably, the compound, hydrate or crystalline form of the invention is formulated into unit dosage forms in order to reduce the amount of drug administered and to obtain dose uniformity. The term "unit dosage form" as used herein refers to physical drug dispersion unit that patients will receive for the appropriate treatment. However, the total daily dosage of the compounds or compositions of the present invention will be determined by the physician based on the reliable range of medical judgment. The specific effective dose level for a particular patient or organism will depend on many factors, including the disease or condition treated and the severity of the disease or condition, the activity of specific compounds, the specific composition, the patient's age, body weight, health status, gender, dietary habits, time of administration, route of administration and excretion rate of the specific compound used, the duration of treatment, drug combination or drug used in tandem with another specific compounds, as well as some other pharmacological factors known in the art.

The amount of the compound, hydrate or crystalline form disclosed herein that may be combined with the carrier materials to produce a composition in a single dosage form will vary depending upon the host treated, the particular mode of administration. In other embodiments, the compositions should be formulated so that a dosage of between 0.01-200 mg/kg body weight/day of the inhibitor can be administered to a patient receiving these compositions.

Compound, hydrate or crystalline form disclosed herein can be administered as the sole pharmaceutical agent or in combination with one or more other additional therapeutic (pharmaceutical) agents where the combination causes no unacceptable adverse effects. This may be of particular relevance for the treatment of hyper-proliferative diseases such as cancer. In this instance, the compound, hydrate or crystalline form disclosed herein can be combined with known cytotoxic agents, signal transduction inhibitors, or with other anti-cancer agents, as well as with admixtures and combinations thereof. As used herein, additional therapeutic agents that are normally administered to treat a particular disease, or condition, are known as "appropriate for the disease, or condition, being treated". As used herein, "additional therapeutic agents" include chemotherapeutic agents and/or other anti-proliferative agents. For example, chemotherapeutic agents or other antiproliferative agents may be combined with the compound, hydrate or crystalline form disclosed herein to treat proliferative disease or cancer.

Examples of chemotherapeutic agents or other antiproliferative agents include HDAC inhibitors including, but not limited to, SAHA, MS-275, MGO 103, and those described in WO 2006/010264, WO 03/024448, WO 2004/069823, US 2006/0058298, US 2005/0288282, WO 00/71703, WO 01/38322, WO 01/70675, WO 03/006652, WO 2004/035525, WO 2005/030705, WO 2005/092899, and demethylating agents including, but not limited to, 5-aza-dC, Vidaza and Decitabine and those described in U.S. Pat. Nos. 6,268,137, 5,578,716, 5,919,772, 6,054,439, 6,184,211, 6,020,318, 6,066,625, 6,506,735, 6,221,849, 6,953,783, U.S. Ser. No. 11/393,380.

In another embodiment disclosed herein, chemotherapeutic agents or other anti-proliferative agents may be combined with the compound, hydrate or crystalline form disclosed herein to treat proliferative diseases and cancer. Examples of known chemotherapeutic agents include, but are not limited to, for example, other therapies or anticancer agents that may be used in combination with the inventive anticancer agents disclosed herein and include surgery, radiotherapy (in but a few examples, gamma-radiation, neutron beam radiotherapy, electron beam radiotherapy, proton therapy, brachytherapy, and systemic radioactive isotopes, to name a few), endocrine therapy, taxanes (taxol, taxotere etc.), platinum derivatives, biologic response modifiers (interferons, interleukins, and tumor necrosis factor (TNF), TRAIL receptor targeting, agents, to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, cyclophosphamide, melphalan, ifosfamide), antimetabolites (methotrexate, pemetrexed etc.), purine antagonists and pyrimidine antagonists (6-mercaptopurine, 5-fluorouracil, cytarabile, gemcitabine), spindle poisons (vinblastine, vincristine, vinorelbine, paclitaxel), podophyllotoxins (etoposide, irinotecan, topotecan), antibiotics (doxorubicin, bleomycin, mitomycin), nitrosoureas (carmustine, lomustine), inorganic ions (cisplatin, carboplatin), cell cycle inhibitors (KSP mitotic kinesin inhibitors, CENP-E and CDK inhibitors), enzymes (asparaginase), and hormones (tamoxifen, leuprolide, flutamide, and megestrol), gleevec, adriamycin, dexamethasone, and cyclophosphamide, antiangiogenic agents (avastin and others). kinase inhibitors (imatinib, sutent, nexavar, erbitux, herceptin, tarceva, iressa and others). Agents inhibiting or activating cancer pathways such as the mTOR, HIF (hypoxia induced factor) pathways and others. For a more comprehensive discussion of updated cancer therapies see, http://www.nci.nih.gov/, a list of the oncology drugs approved by FDA shown in http://www.fda.gov/cder/cancer/druglistrame.htm, and The Merck Manual, Eighteenth Ed. 2006, the entire contents of which are hereby incorporated by reference.

In another embodiment, the compound, hydrate or crystalline form disclosed herein can be combined with cytotoxic anti-cancer agents. Examples of such agents can be found in the 13th Edition of the Merck Index (2001). These agents include, by no way of limitation, asparaginase, bleomycin, carboplatin, carmustine, chlorambucil, cisplatin, colaspase, cyclophosphamide, cytarabine, dacarbazine, dactinomycin, daunorubicin, doxorubicin (adriamycin), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, or vindesine.

Other cytotoxic drugs suitable for use with the compound, hydrate or crystalline form disclosed herein include, but are not limited to, those compounds acknowledged to be used in the treatment of neoplastic diseases, such as those for example in Goodman and Gilman's, The Pharmacological Basis of Therapeutics (Ninth Edition, 1996, McGraw-Hill). These agents include, by no way of limitation, aminoglutethimide, L-asparaginase, azathioprine, 5-azacytidine, cladribine, busulfan, diethylstilbestrol, 2',2'-difluorodeoxycytidine, docetaxel, erythro hydroxy nonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-Laspartate (PALA), plicamycin, semustine, teniposide, testosterone propionate, thiotepa, trimethylmelamine, uridine or vinorelbine.

Other cytotoxic anti-cancer agents suitable for use in combination with the compound, hydrate or crystalline form disclosed herein also include newly discovered cytotoxic principles, some examples of cytotoxic principles include, but are not limited to, oxaliplatin, gemcitabine, capecitabine, macrolide and its natural or synthetic derivatives, temozolomide (Quinn et al., J Clin. Oncology, 2003, 21(4), 646-651), tositumomab (BEXXAR®), trabectedin (Vidal et al., *Proceedings of the American Society for Clinical Oncology*, 2004, 23, abstract, 3181), and the inhibitors of the kinesin spindle protein Eg5 (Wood et al., Curr. Opin. Pharmacol. 2001, 1, 370-377).

In another embodiment, the compound, hydrate or crystalline form disclosed herein can be combined with other signal transduction inhibitors. The other signal transduction inhibitors can also target the EGFR family, such as EGFR, HER-2, and HER-4 (Raymond et al., *Drugs*, 2000, 60 (Suppl. 1), 15-23; Harari et al., *Oncogene*, 2000, 19 (53), 6102-6114), and their respective ligands. Examples of such agents include, by no way of limitation, antibody therapies such as HERCEPTIN® (trastuzumab), erbitux, and pertuzumab. Examples of such agents include, by no way of limitation, small-molecule kinase inhibitors such as IRESSA® (Gefitinib), TARCEVA® (Erlotinib), TYKERB® (Lapatinib), Canertinib (CI1033), AEE788 (Traxler et al., *Cancer Research*, 2004, 64, 4931-4941).

In another embodiment, the compound, hydrate or crystalline form disclosed herein can be combined with other signal transduction inhibitors targeting receptor kinases of the split-kinase domain families (VEGFR, FGFR, PDGFR, flt-3, c-kit, c-fms, and the like), and their respective ligands. These agents include, by no way of limitation, antibodies such as AVASTIN® (bevacizumab). These agents also include, by no way of limitation, small-molecule inhibitors such as Gleevec/Imanitib, Sprycel (Dasatinib), Tasigna/Nilotinib, Nexavar(Vandetanib), Vatalanib (PTK787/ZK222584) (Wood et al., *Cancer Res.* 2000, 60(8), 2178-2189), Telatinib/BAY-57-9352, BMS-690514, BMS-540215, Axitinib/AG-013736, Motesanib/AMG706, Sutent/Sunitinib/SU-11248, ZD-6474 (Hennequin et al., *92nd AACR Meeting*, New Orleans, Mar. 24-28, 2001, abstract 3152), KRN-951 (Taguchi et al., *95th AACR Meeting*, Orlando, Fla., 2004, abstract 2575), CP-547,632 (Beebe et al., *Cancer Res.* 2003, 63, 7301-7309), CP-673,451 (Roberts et al., *Proceedings of the American Association of Cancer Research*, 2004, 45, abstract 3989), CHIR-258 (Lee et al., *Proceedings of the American Association of Cancer Research*, 2004, 45, abstract 2130), MLN-518 (Shen et al., *Blood*, 2003, 102, 11, abstract 476).

In another embodiment, the compound, hydrate or crystalline form disclosed herein can be combined with inhibitors of histone deacetylase. Examples of such agents include, by no way of limitation, suberoylanilide hydroxamic acid (SAHA), LAQ-824 (Ottmann et al., *Proceedings of the American Society for Clinical Oncology*, 2004, 23, abstract 3024), LBH-589 (Beck et al., *Proceedings of the American Society for Clinical Oncology*, 2004, 23, abstract 3025), MS-275 (Ryan et al., *Proceedings of the American Association of Cancer Research*, 2004, 45, abstract 2452), FR-901228 (Piekarz et al., *Proceedings of the American Society for Clinical Oncology*, 2004, 23, abstract 3028) and MGCDOI 03 (U.S. Pat. No. 6,897,220).

In another embodiment, the compound, hydrate or crystalline form disclosed herein can be combined with other anti-cancer agents such as proteasome inhibitors, and m-TOR inhibitors. These include, by no way of limitation, bortezomib (Mackay et al., *Proceedings of the American Society for Clinical Oncology*, 2004, 23, Abstract 3109), and CCI-779 (Wu et al., *Proceedings of the American Association of Cancer Research*, 2004, 45, abstract 3849). In another embodiment, the compound, hydrate or crystalline form disclosed herein can be combined with other anti-cancer agents such as topoisomerase inhibitors, including but not limited to camptothecin.

Those additional agents may be administered separately from the compound, hydrate or crystalline form disclosed herein as part of a multiple dosage regimen. Alternatively, those agents may be part of a single dosage form, mixed together with the compound, hydrate or crystalline form disclosed herein in a single composition. If administered as part of a multiple dosage regimen, the two active agents may be submitted simultaneously, sequentially or within a period of time from one another which would result in the desired activity of the agents.

The amount of both the compound and the additional therapeutic agent (in those compositions which comprise an additional therapeutic agent as described above) that may be combined with the carrier materials to produce a single dosage form will vary depending upon the host treated and the particular mode of administration. Normally, the amount of additional therapeutic agent present in the compositions disclosed herein will be no more than the amount that would normally be administered in a composition comprising that therapeutic agent as the only active agent. In other embodiments, the amount of additional therapeutic agent in the presently disclosed compositions will range from about 50% to 100% of the amount normally present in a composition comprising that agent as the only therapeutically active agent. In those compositions which comprise an additional therapeutic agent, that additional therapeutic agent and the compound disclosed herein may act synergistically.

The invention features pharmaceutical compositions that include one or more compound or hydrate disclosed herein, or one or more crystalline forms disclosed herein, or a combination thereof, and a pharmaceutically acceptable carrier, adjuvant, or vehicle. The amount of compositions disclosed herein is effective to detectably inhibit a protein kinase, such as EGFR inhibitory activity. The compositions disclosed herein are useful in therapy as antineoplasia agents or to minimize deleterious effects of EGFR.

Compositions disclosed herein would be useful for, but are not limited to, the prevention or treatment of proliferative diseases, conditions, or disorders in a patient by administering to the patient a composition disclosed herein in an effective amount. Such diseases, conditions, or disorders include cancer, particularly metastatic cancer, non-small cell lung cancer and epidermoid carcinoma.

Compositions disclosed herein would be useful for the treatment of neoplasia including cancer and metastasis, including, but not limited to: carcinoma such as cancer of the epidermis, bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocytic leukemia, acute lymphoblastic leukemia, B-cell lymphoma, T-cell lymphoma, Hodgkin's lymphoma, non-Hodgkin's lymphoma, hairy cell leukemia and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

The compositions also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemangioendothelioma, angiofibroma of the nasopharynx and avascular necrosis of bone; and disorders of the female reproductive system such as endometriosis. The compounds are also useful for the treatment of edema, and conditions of vascular hyperpermeability.

The compositions disclosed herein are also useful in the treatment of diabetic conditions such as diabetic retinopathy and microangiopathy. The compounds disclosed herein are also useful in the reduction of blood flow in a tumor in a subject. The compositions disclosed herein are also useful in the reduction of metastasis of a tumor in a subject.

Besides being useful for human treatment, these compositions are also useful for veterinary treatment of animals such as companion animals, exotic animals and farm animals, including mammals, rodents, and the like. In other embodiments, the animals disclosed herein include horses, dogs, and cats. As used herein, the compositions disclosed herein include the pharmaceutically acceptable derivatives thereof.

Where the plural form is used for compounds, salts, and the like, this is taken to refer to also a single compound, salt, and the like.

The treatment method that includes administering a composition disclosed herein can further include administering to the patient an additional therapeutic agent (combination therapy) selected from: a chemotherapeutic or anti-proliferative agent, or an anti-inflammatory agent, wherein the additional therapeutic agent is appropriate for the disease being treated and the additional therapeutic agent is administered together with a composition disclosed herein as a single dosage form or separately from the composition as part of a multiple dosage form. The additional therapeutic agent may be administered simultaneously or sequentially with the composition disclosed herein.

The invention also features a method of inhibiting the growth of a cell that expresses EGFR, which includes contacting the cell with a composition disclosed herein, thereby causing inhibition of growth of the cell. Examples of a cell whose growth can be inhibited include: a epidermoid carcinoma cell, a breast cancer cell, a colorectal cancer cell, a lung cancer cell, a papillary carcinoma cell, a prostate cancer cell, a lymphoma cell, a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell, or a leukemia cell.

Provided herein is a method of inhibiting EGFR kinase activity in a biological sample that includes contacting the biological sample with a composition disclosed herein. The term "biological sample" as used herein, means a sample outside a living organism and includes, without limitation, cell cultures or extracts thereof; biopsied materials obtained from a mammal or extracts thereof; and blood, saliva, urine, feces, semen, tears, or other body fluids or extracts thereof. Inhibition of kinase activity, particularly EGFR kinase activity, in a biological sample is useful for a variety of purposes known to one of skill in the art. Examples of such purposes include, but are not limited to, blood transfusion, organ-transplantation, biological specimen storage, and biological assays.

An "effective amount" or "effective dose" of the pharmaceutically acceptable composition is an amount that is effective in treating or lessening the severity of one or more of the aforementioned disorders. The compositions, according to the method disclosed herein, may be administered using any amount and any route of administration which is effective for treating or lessening the severity of the disorder or disease. The exact amount required will vary from subject to subject, depending on the species, age, and general condition of the subject, the severity of the infection, the particular agent, its mode of administration, and the like. A composition can also be administered with one or more other therapeutic agents as discussed above.

The pharmaceutical composition disclosed herein may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound disclosed herein.

Suitable coatings and the general preparation of coated implantable devices are described in U.S. Pat. Nos. 6,099,562, 5,886,026, and 5,304,121, the contents of each of which are incorporated by reference herein. The coatings are typically biocompatible polymeric materials such as a hydrogel polymer, polymethyldisiloxane, polycaprolactone, polyethylene glycol, polylactic acid, ethylene-vinyl acetate, and mixtures thereof. The coatings may optionally be further covered by a suitable topcoat of fluorodimethicone, poly-saccharide enzymes, polyethylene glycol, phospholipids or combinations thereof to impart controlled release characteristics of the composition. Implantable devices coated with a composition disclosed herein are another embodiment disclosed herein. The pharmaceutical composition may also be coated on implantable medical devices, such as beads, or co-formulated with a polymer or other molecule, to provide a "drug depot" thus permitting the drug to be released over a longer time period than administration of an aqueous solution of the drug.

DESCRIPTION OF THE PREFERRED EMBODIMENTS

The invention is further illustrated by the following examples, which are not be construed as limiting the invention in scope.

The X-Ray powder Diffraction (XRPD) analysis method of the present invention examples comprises recording an X-ray powder diffraction diagram on a PANalytical Empyrean X-ray diffractometer using Cu-Kα radiation (45 KV, 40 mA). A thin layer is prepared from powder sample on the single-crystal silicon wafer, and a sample spinner is used. The angular range extends from 3° to 40° in 2θ with a 0.0168° step size in 2θ. Data are collected by Data Collector software, and processed by HighScore Plus software, read by Data Viewer software.

Thermogravimetric Analysis (TGA): Thermogravimetric curve is recorded on a TA Q500 instrument with a thermo-analysis controller. The data are collected and analyzed by TA Instruments Thermal Solutions software. About 10 mg sample is weighed accurately in platinum sample pans, then heated from ambient temperature to 350° C. using a linear heating device at a scan rate of 10° C./minute for sample analysis. During the period of sample analysis, TGA furnace chamber is purged by dry nitrogen.

X-Ray Single-crystal diffractometer of the present invention examples: Single-crystal X-ray diffraction pattern is recorded on an Agilent Technologies Gemini A Ultra X-ray diffractometer using Cu-Kα radiation (40 KV, 40 mA) and w-scan, the total number of diffraction counts is 1145, analyzing the crystallography data tables and single-crystal structure by SHELXTL software.

The purity of the compound used in the stability test or accelerated test is measured by Aglient 1200 high performance liquid chromatography with VWD detector. The chromatographic column model is ZORBAX Extend-C18 (4.6×150 mm, 5 µM), the detection wavelength is 250 nm, the flow rate is 1.0 mL/min, the column temperature is 40° C., and the mobile phase is 10 mM $KH_2PO_4$ (pH=7.5)-acetonitrile (v/v=55/45).

The preparation method of crystalline form I and experimental evaluation of crystalline form I will be described detailedly below.

The specific preparation method of 4-[(3-chloro-4-fluorophenyl)amino]-7-methoxy-6-[3-[(1R,6S)-2,5-dioxa-8-azabicyclo[4.3.0]nonan-8-yl]propoxy]quinazoline can refer to the preparation method of example 6 disclosed in patent CN 103102344 A (publication number).

Example 1

1. Preparation of crystalline form I of 4-[(3-chloro-4-fluorophenyl)amino]-7-methoxy-6-[3-[(1R,6S)-2,5-dioxa-8-azabicyclo[4.3.0]nonan-8-yl]propoxy]quinazoline dimethanesulfonate monohydrate To a solution of methanesulfonic acid (0.173 g, 1.803 mmol) in methanol (10 mL) was added a solution of 4-[(3-chloro-4-fluorophenyl)amino]-7-methoxy-6-[3-[(1R,6S)-2,5-dioxa-8-azabicyclo[4.3.0]nonan-8-yl]propoxy]quinazoline (0.40 g, 0.819 mmol) in methanol (30 mL) at rt. The mixture was stirred at 60° C. overnight. The mixture was concentrated in vacuo to remove the solvent. The residue was triturated by a large amount of ethyl acetate to give a white solid (519 mg, 93.01%).

2. Identification of crystalline form I of 4-[(3-chloro-4-fluorophenyl)amino]-7-methoxy-6-[3-[(1R,6S)-2,5-dioxa-8-azabicyclo[4.3.0]nonan-8-yl]propoxy]quinazoline dimethanesulfonate monohydrate 1) The salt-forming ratio was 1:2 determined by $^1$H NMR.

2) The XRPD pattern analyzed and identified by using Empyrean X-ray powder diffraction (XRPD) with Cu-Kα radiation had the following characteristic peaks expressed in degrees 2θ at 6.36°, 6.66°, 9.47°, 10.82°, 11.70°, 13.31°, 14.88°, 15.86°, 16.58°, 17.15°, 17.46°, 18.05°, 19.30°, 20.46°, 20.84°, 21.34°, 21.76°, 22.28°, 22.71°, 23.16°, 24.07°, 24.39°, 25.18°, 25.46°, 26.29°, 26.78°, 27.15°, 28.01°, 28.80°, 29.77°, 30.44°, 31.06°, 32.05°, 33.01°, 33.51°, 33.84°, 34.90°, 38.03°, 38.58° and 39.48°. The error margin in 2θ of the characteristic peaks was ±0.2° (as shown in FIG. 1).

3) The TGA curve was analyzed and identified by using TA Q500 thermal gravity analysis (TGA) with a scan rate of 10° C./minute at a temperature range of 25° C.~150° C., the weight loss ratio was 3.234%. The error margin in the weight loss ratio was ±0.1%; the sample lost crystal water at a temperature range of 79° C.~161° C., and the loss weight was consistent with the theoretical value of crystallization water content (2.577%) (as shown in FIG. 2).

4) The parameters of the single monocrystalline measured by detection of monocrystalline were listed in table 1, and the monocrystalline structure was as shown in FIG. 3.

TABLE 1

The parameters of the single monocrystalline

| | |
|---|---|
| Crystallographic System: | monoclinic system |
| Space Groups: | C2/c |
| Cell Parameters: | a = 27.3004(5) Å, α = 90°, |
| | b = 16.2882(3) Å, β = 103.3439(17)°, |
| | c = 14.3529(2) Å, γ = 90° |
| Volume: | 6210.01(18) Å$^3$ |
| Molecules number of each unit cell (Z): | 8 |

Example 2 Pharmacokinetic Assay

The pharmacokinetic properties of the compound of Formula (II) and crystalline form I of the invention were assessed in beagle dogs: each group having 3 beagle dogs was administered by oral in a capsule form. The dosage amount of crystalline form I was converted and determined according to the compound of Formula (II) at a dosage of 5 mg/kg. Results were as shown below.

TABLE 2

In vivo Pharmacokinetic parameters of beagle dogs

| Compound | $T_{max}$ (h) | $C_{max}$ (ng/ml) | $AUC_{last}$ (ng · h/ml) | $AUC_{inf}$ (ng · h/ml) | $T_{1/2}$ (h) |
|---|---|---|---|---|---|
| Compound of Formula (II) | 1.67 | 125.37 | 825.31 | 886.11 | 3.62 |
| Crystalline form I | 1.33 | 231.43 | 1446.44 | 1465.11 | 3.65 |

Conclusion: crystalline form I of 4-[(3-chloro-4-fluorophenyl)amino]-7-methoxy-6-[3-[(1R,6S)-2,5-dioxa-8-azabicyclo[4.3.0]nonan-8-yl]propoxy]quinazoline dimethanesulfonate monohydrate had better bioavailability than compound of Formula (II). Individual data analysis of beagle dog showed that crystalline form I had a higher exposure level and a faster absorption in dogs, and the Tmax time of crystalline form I was earlier than compound of Formula (II).

Example 3 Hygroscopic Test

1. Instruments: one hundred thousandth electronic balance, type: XP205DR, manufacturer: Mettler.

2. Test method deriving from Chinese Pharmacopoeia 2010, appendix XIX J: Guideline on pharmaceutical hygroscopic test. Specific method is described as follows:

1) Placing a dried glass-stoppered, weighing bottle (outer diameter: 50 mm, height: 15 mm) in a thermostatic drier with saturated aqueous ammonium chloride or ammonium sulfate solution in the bottom at the previous day of the test maintaining the temperature at 25° C.±1° C., and the glass-stoppered, weighing bottle was weighed precisely.

2) Taking and weighing an appropriate amount of the sample ($m_1$), and placing the sample into the weighing bottle with thickness of about 1 mm.

3) Opening the weighing bottle, and placing the glass stopper with the opened weighing bottle in a constant temperature and humidity condition for 24 h.

4) Sealing the weighing bottle with glass stopper, and the weighing bottle sealed with glass stopper was weighed precisely ($m_2$). The percentage (%) of weight gain was calculated.

Percentage (%) of weight gain=$(m_2-m_1-m_0)/m_1 \times 100\%$

5) The hygroscopic features and definition of hygroscopic weight gain are summarized in table 3 (deriving from Chinese Pharmacopoeia 2010, appendix XIX J: Guideline on pharmaceutical hygroscopic test, test conditions: 25° C.±1° C., Relative Humidity 80%±2%).

TABLE 3

The hygroscopic features and definition of hygroscopic weight gain

| | Hygroscopic features | The percentage (%) of hygroscopic weight gain |
|---|---|---|
| 1 | Deliquescence | Absorbing enough water to form liquid |
| 2 | High hygroscopicity | The weight increase of the hygroscopicity is no less than 15% |
| 3 | Having hygroscopicity | The weight increase of the hygroscopicity is between 15% and 2% |
| 4 | Slight hygroscopicity | The weight increase of the hygroscopicity is between 2% and 0.2% |
| 5 | No or almost no hygroscopicity | The weight increase of the hygroscopicity is no less than 0.2% |

3. Results

The results were shown in table 4.

TABLE 4

Hygroscopic test results

| $m_0$ (g) | $m_1$ (g) | $m_2$ (g) | Hygroscopic weight gain |
|---|---|---|---|
| 30.51893 | 0.99751 | 31.51718 | 0.074% |

Conclusion: The weight of crystalline form I of 4-[(3-chloro-4-fluorophenyl)amino]-7-methoxy-6-[3-[(1R,6S)-2,5-dioxa-8-azabicyclo[4.3.0]nonan-8-yl]propoxy]quinazoline dimethanesulfonate monohydrate gained 0.074% after placing crystalline form I at a relative humidity of 80%±2% for 24 h. According to the definition of hygroscopic weight gain, crystalline form I has almost no hygroscopicity.

Example 4 Stability Test

According to "Guidelines for the stability test of raw materials and preparations" (*Chinese Pharmacopoeia*, 2015, *4th edition, general rules* 9001), the stability of crystalline form I was tested as follows:

Appropriate amount of sample was taken into the flat weighing bottle to form a thin layer of no more than 5 mm thick. Then the stability of crystalline form I was tested under the conditions showed in table 5. The content of impurities was tested by HPLC.

TABLE 5

Stability test method

| Project | Test condition | sampling point | Inspection project |
|---|---|---|---|
| High temperature | 60° C. ± 2° C. | 0, 5, 10 days | Impurities |

TABLE 5-continued

Stability test method

| Project | Test condition | sampling point | Inspection project |
|---|---|---|---|
| High humidity | 25° C. ± 2° C./92.5% RH | 0, 5, 10 days | |
| Illumination | Visible light illumination: 4500 ± 500 lx, UV intensity: not less than 0.7 W·h/m² | 0, 5, 10, 15 days | |

The results were shown in table 6.

TABLE 6

The results of stability test

| Condition | | | High temperature | | High humidity | | Illumination | | |
|---|---|---|---|---|---|---|---|---|---|
| Project | 0 day | 5 days | 10 days | 5 days | 10 days | 5 days | 10 days | 15 days |
| Crystalline form I Impurities (total impurities, %) | 0.13 | 0.12 | 0.14 | 0.14 | 0.16 | 0.13 | 0.13 | 0.14 |

Conclusion: The impurity of crystalline form I of 4-[(3-chloro-4-fluorophenyl)amino]-7-methoxy-6-[3-[(1R,6S)-2,5-dioxa-8-azabicyclo[4.3.0]nonan-8-yl]propoxy]quinazoline dimethanesulfonate monohydrate had no obvious change at high temperature for 10 days, or under high humidity for 10 days or under illumination condition for 15 days, thereby the quality of crystalline form I is stable under high temperature condition, high humidity condition or illumination condition.

Example 5 Accelerated Test

According to "Guidelines for the stability test of raw materials and preparations" (*Chinese Pharmacopoeia*, 2015, *4th edition, general rules* 9001), the accelerated test of crystalline form I was practiced as follows:

Medicinal low density polyethylene bag (the size was 140*120*0.104 mm³, the manufacture was Tianjin Litian Medicine Packing Material Co., Ltd, and the batch number was 121238.) was used as inner package material, and the bag was sealed by nylon cable ties; and paper tube was used as a packaging material. The packaged samples were placed in a constant temperature and humidity test chamber (40±2° C./75%±5% RH) for six months for accelerated test. Sampling at the end of 1, 2, 3 or 6 months for testing the moisture content of the sample by using karl fischer titration, the content of impurities was measured by HPLC.

The test results were shown in table 7.

TABLE 7

Results of Accelerated test

| | Project | Moisture (%) | Impurities (total impurities, %) |
|---|---|---|---|
| Time | 0 day | 2.79 | 0.18 |
| | One month | 2.92 | 0.18 |
| | Two months | 2.87 | 0.17 |
| | Three months | 3.09 | 0.18 |
| | Six months | 2.86 | 0.17 |

Conclusions:

(1) Impurity had no obvious change in the progress of accelerated test, and the property of sample was stable under the packaging condition, without degradation.

(2) Moisture had no obvious change in the progress of accelerated test, and the sample wasn't hygroscopic under the packaging condition.

The results of the accelerated test showed that, the quality of crystalline form I of 4-[(3-chloro-4-fluorophenyl)amino]-7-methoxy-6-[3-[(1R,6S)-2,5-dioxa-8-azabicyclo[4.3.0] nonan-8-yl]propoxy]quinazoline dimethanesulfonate monohydrate was stable under the accelerated test condition for six months using medicinal low density polyethylene bag as inner package material.

The foregoing has described the invention including basic instructions. Any equivalent alterations according the technology of the present invention that would be apparent to the skilled person are within the scope of the invention.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (I):

2. A hydrate of a compound having formula (I).

3. The hydrate of claim 2, wherein the hydrate is a monohydrate of the compound having formula (I).

4. A crystalline form of a monohydrate of a compound having formula (I):

wherein the crystalline form is form I having one or more of following characteristics:
i) an X-ray powder diffraction (XRPD) pattern comprising peaks expressed in degrees 2θ at 14.88°±0.2°, 18.05°±0.2°, 20.84°±0.2°, 21.34°±0.2°, 24.39°±0.2° and 25.18°±0.2°; or/and
ii) the following structure parameters analyzed from monocrystalline:

| | |
|---|---|
| Crystallographic System: | monoclinic system |
| Space Groups: | C2/c; |
| Cell Parameters: | a = 27.3004(5) Å, α = 90°, |
| | b = 16.2882(3) Å, β = 103.3439(17)°, |
| | c = 14.3529(2) Å, γ = 90°; |
| Volume: | 6210.01(18) Å$^3$; |
| Molecules number of each unit cell (Z): | 8. |

5. The crystalline form of claim 4 having an X-ray powder diffraction (XRPD) pattern comprising peaks expressed in degrees 2θ at 9.47°±0.2°, 14.88°±0.2°, 16.58°±0.2°, 17.15°±0.2°, 17.46°±0.2°, 18.05°±0.2°, 20.46°±0.2°, 20.84°±0.2°, 21.34°±0.2°, 22.71°±0.2°, 23.16°±0.2°, 24.39°±0.2°, 25.18°±0.2°, 25.46°±0.2°, 26.29°±0.2° and 28.01°±0.2°.

6. The crystalline form of claim 4 having an X-ray powder diffraction (XRPD) pattern comprising expressed in degrees 2θ at 6.36°±0.2°, 6.66°±0.2°, 9.47°±0.2°, 10.82°±0.2°, 11.70°±0.2°, 13.31°±0.2°, 14.88°±0.2°, 15.86°±0.2°, 16.58°±0.2°, 17.15°±0.2°, 17.46°±0.2°, 18.05°±0.2°, 19.30°±0.2°, 20.46°±0.2°, 20.84°±0.2°, 21.34°±0.2°, 21.76°±0.2°, 22.28°±0.2°, 22.71°±0.2°, 23.16°±0.2°, 24.07°±0.2°, 24.39°±0.2°, 25.18°±0.2°, 25.46°±0.2°, 26.29°±0.2°, 26.78°±0.2°, 27.15°±0.2°, 28.01°±0.2°, 28.80°±0.2°, 29.77°±0.2°, 30.44°±0.2°, 31.06°±0.2°, 32.05°±0.2°, 33.01°±0.2°, 33.51°±0.2°, 33.84°±0.2°, 34.90°±0.2°, 38.03°±0.2°, 38.58°±0.2° and 39.48°±0.2°.

7. The crystalline form of claim 4 having an X-ray powder diffraction (XRPD) pattern as shown in FIG. 1.

8. The crystalline form of claim 4 having a monocrystalline structure as shown in FIG. 3.

9. A pharmaceutical composition comprising the compound of claim 1, and a pharmaceutically acceptable carrier, excipient, diluent, adjuvant, vehicle or a combination thereof.

10. The pharmaceutical composition of claim 9 further comprising a therapeutic agent, wherein the therapeutic agent is a chemotherapeutic agent used for treating proliferative disease or cancer, an antiproliferative agent, a cytotoxic agent, a signal transduction inhibitor, an agent used for treating non-small cell lung cancer or skin cancer or a combination thereof; and wherein the therapeutic agent is adriamycin, rapamycin, temsirolimus, everolimus, ixabepilone, gemcitabine, cyclophosphamide, dexamethasone, etoposide, fluorouracil, imatinib mesylate, dasatinib, nilotinib, erlotinib, lapatinib, gefitinib, sorafenib, sunitinib, interferon, carboplatin, topotecan, paclitaxel, vinblastine, vincristine, temozolomide, tositumomab, trabedectin, bevacizumab, trastuzumab, cetuximab, panitumumab, icotinib, icotinib hydrochloride, matuzmab, neratinib, canertinib, vandetanib, cediranib, vatalanib, axitinib, motesanib, nimotuzumab, theliatinib, epitinib, simotinib, poziotinib, varlitinib, rociletinib, pelitinib, osimertinib, PKI-166, PD 158780, MDX447, Mab425, HM-61713, TAS-121, seribantumab, naquotinib, or a combination thereof.

11. A method of inhibiting EGFR in a subject, comprising administering to the subject a therapeutically effective amount of the compound of claim 1.

12. A method of treating a proliferative disorder in a patient, comprising administering to the patient a therapeutically effective amount of the compound of claim 1; wherein the proliferative disorder is colon cancer lung cancer or malignant glioma.

13. A pharmaceutical composition comprising the hydrate of claim 2; and a pharmaceutically acceptable carrier, excipient, diluent, adjuvant, vehicle or a combination thereof.

14. A pharmaceutical composition comprising the crystalline form of claim 4; and a pharmaceutically acceptable carrier, excipient, diluent, adjuvant, vehicle or a combination thereof.

15. The pharmaceutical composition of claim 13 further comprising a therapeutic agent, wherein the therapeutic agent is a chemotherapeutic agent used for treating proliferative disease or cancer, an antiproliferative agent, a cytotoxic agent, a signal transduction inhibitor, an agent used for treating non-small cell lung cancer or skin cancer or a combination thereof; and wherein the therapeutic agent is adriamycin, rapamycin, temsirolimus, everolimus, ixabepilone, gemcitabine, cyclophosphamide, dexamethasone, etoposide, fluorouracil, imatinib mesylate, dasatinib, nilotinib, erlotinib, lapatinib, gefitinib, sorafenib, sunitinib, interferon, carboplatin, topotecan, paclitaxel, vinblastine, vincristine, temozolomide, tositumomab, trabedectin, bevacizumab, trastuzumab, cetuximab, panitumumab, icotinib, icotinib hydrochloride, matuzmab, neratinib, canertinib, vandetanib, cediranib, vatalanib, axitinib, motesanib, nimotuzumab, theliatinib, epitinib, simotinib, poziotinib, varlitinib, rociletinib, pelitinib, osimertinib, PKI-166, PD 158780, MDX447, Mab425, HM-61713, TAS-121, seribantumab, naquotinib, or a combination thereof.

16. The pharmaceutical composition of claim 14 further comprising a therapeutic agent, wherein the therapeutic agent is a chemotherapeutic agent used for treating proliferative disease or cancer, an antiproliferative agent, a cytotoxic agent, a signal transduction inhibitor, an agent used for treating non-small cell lung cancer or skin cancer or a combination thereof; and wherein the therapeutic agent is adriamycin, rapamycin, temsirolimus, everolimus, ixabepilone, gemcitabine, cyclophosphamide, dexamethasone, etoposide, fluorouracil, imatinib mesylate, dasatinib, nilotinib, erlotinib, lapatinib, gefitinib, sorafenib, sunitinib, interferon, carboplatin, topotecan, paclitaxel, vinblastine, vincristine, temozolomide, tositumomab, trabedectin, bevacizumab, trastuzumab, cetuximab, panitumumab, icotinib, icotinib hydrochloride, matuzmab, neratinib, canertinib, vandetanib, cediranib, vatalanib, axitinib, motesanib, nimotuzumab, theliatinib, epitinib, simotinib, poziotinib, varlitinib, rociletinib, pelitinib, osimertinib, PKI-166, PD 158780, MDX447, Mab425, HM-61713, TAS-121, seribantumab, naquotinib, or a combination thereof.

17. A method of inhibiting EGFR in a subject, comprising administering to the subject a therapeutically effective amount of the crystalline form of claim 4.

18. A method of inhibiting EGFR in a subject, comprising administering to the subject a therapeutically effective amount of the pharmaceutical composition of claim 14.

19. A method of treating the severity of a proliferative disorder in a patient, comprising administering to the patient a therapeutically effective amount of the crystalline form of claim 4, wherein the proliferative disorder is colon cancer lung cancer, or malignant glioma.

20. A method of treating a proliferative disorder in a patient, comprising administering to the patient a therapeutically effective amount of the pharmaceutical composition of claim 14; wherein the proliferative disorder is colon cancer, lung cancer, or malignant glioma.

\* \* \* \* \*